United States Patent [19]

Ogawa et al.

[11] Patent Number: 5,262,296

[45] Date of Patent: Nov. 16, 1993

[54] FREEZE-DRIED COMPOSITION CONTAINING ENZYME-LABELED ANTI-HUMAN INTERFERON-$\beta$ ANTIBODY AND ENZYME IMMUNOASSAY KIT CONTAINING THE COMPOSITION

[75] Inventors: Etsuko Ogawa; Shojiro Yamazaki, both of Kamakura, Japan

[73] Assignee: Toray Industries, Inc., Japan

[21] Appl. No.: 445,624

[22] PCT Filed: Mar. 29, 1989

[86] PCT No.: PCT/JP89/00329

§ 371 Date: Jan. 4, 1990

§ 102(e) Date: Jan. 4, 1990

[87] PCT Pub. No.: WO89/09402

PCT Pub. Date: Oct. 5, 1989

[30] Foreign Application Priority Data

Mar. 30, 1988 [JP] Japan .................................. 63-76881

[51] Int. Cl.$^5$ ............................................. G01N 33/53
[52] U.S. Cl. ..................... 435/7.94; 435/962; 435/963; 435/975; 436/518; 436/548; 436/512; 436/826
[58] Field of Search ..................... 435/7.94, 28, 4, 188, 435/810, 811, 962, 963, 975; 436/5, 518, 548, 808, 810, 815, 826, 512

[56] References Cited

U.S. PATENT DOCUMENTS 4,880,751 11/1989 Georhegan ........................ 436/518
4,931,385 6/1990 Block et al. ...................... 435/7.94

FOREIGN PATENT DOCUMENTS

| 0111216 | 6/1984 | European Pat. Off. . |
| 0140489 | 5/1985 | European Pat. Off. . |
| 59-144796 | 8/1984 | Japan . |
| 60-149972 | 8/1985 | Japan . |
| 62-206447 | 9/1987 | Japan . |
| 8201773 | 5/1982 | PCT Int'l Appl. . |
| 8700196 | 1/1987 | PCT Int'l Appl. . |

OTHER PUBLICATIONS

Sano et al., J. Immunol. Meth. 64:31–37, 1983.
Yamazaki et al., J. Immunoassay 10(1):57–73, 1989.

*Primary Examiner*—Esther L. Kepplinger
*Assistant Examiner*—Donna C. Wortman
*Attorney, Agent, or Firm*—Austin R. Miller

[57] ABSTRACT

The present invention relates to the stabilization of enzyme-labeled anti-human interferon-$\beta$ antibody for use in an enzyme immunoassay of human interferon-$\beta$ and provides a freeze-dried composition containing an anti-human interferon-$\beta$ antibody which has been freeze-dried in the presence of trehalose as a nonreducing disaccharide. The freeze-dried composition according to the present invention whose reduction in enzymatic activity remains minimized even when stored for a long period of time is conveniently incorporated into an EIA kit. No conventional non-volatile buffer solution such as a phosphate buffer solution is added to the original freeze-dried liquid of the present invention.

14 Claims, 2 Drawing Sheets

FREEZE-DRIED COMPOSITION CONTAINING ENZYME-LABELED ANTI-HUMAN INTERFERON-β ANTIBODY AND ENZYME IMMUNOASSAY KIT CONTAINING THE COMPOSITION

BACKGROUND OF THE INVENTION

1. Field of the Invention

The present invention relates to the stabilization of an enzyme-labeled anti-human interferon-β antibody which may be used for an immunological microassay of human interferon-β, and more particularly to a freeze-dried composition which is capable of stabilizing an enzyme-labeled anti-human interferon-β antibody over a long period of time. The present invention further relates to an enzyme immunoassay kit comprising such a freeze-dried composition.

2. Prior Art

When a trace amount of substance such as a protein, a peptide hormone etc. contained in a biological material such as serum, urine or the like will be measured, the method for measuring it requires a high sensitivity and high specificity. As a method for measuring used for this purpose, an immunoassay which utilizes an antigen-antibody reaction is well known.

The immunoassay may be classified into a competitive method and a non-competitive method. In the former, a sample liquid to be measured containing the antigen or antibody, which is a substance to be measured, is mixed with a substance to be measured which was pre-labeled and had a known concentration, and then the antibody or antigen is added to the mixture to form an antigen-antibody complex. By measuring a ratio of the labeled substance to be measured and the substance to be measured, each of which was involved in the complex formation, a content of the substance to be measured can be calculated. In the latter method known as a sandwich method, on the other hand, a first antibody is first bound to a solid phase, and then a sample liquid to be measured containing an antigen, which is a substance to be measured, is brought into contact therewith to bind the antigen to the first antibody on the solid phase, the solid phase being thereafter separated from the liquid phase. By the antigen-antibody reaction, a labeled second antibody is then bound to the antigen which is a substance to be measured and has been bound to the first antibody on the solid phase, and thereby an amount of the antigen to be measured can be determined after measuring an amount of the bound labeled antibody.

In accordance with the labeled substance used, the immunoassay may be divided into, for example, radio immunoassay utilizing a labeling agent of radioactive substance and enzyme immunoassay utilizing a labeling agent of enzyme. The enzyme immunoassay has recently come into wide use for such as ordinary clinical examinations because the assay has a sufficiently measurable sensitivity and a simple operability and is exempt from troublesome disposal after use.

However, an enzyme-labeled antibody or antigen has a problem of the long-term stability in a freeze-dried state for practical use. Therefore, the development of an enzyme-labeled antibody or enzyme-labeled antigen in which the enzyme activity is not lowered during the long storage has been demanded. Generally, an activity which is determined immediately after the preparation of the enzyme-labeled anti-human interferon-β antibody as the enzyme-labeled antibody is lost by 50% at room temperature about 2 days after the preparation thereof, and substantially all the activity is lost 7 days thereafter.

SUMMARY OF THE INVENTION

It is an object of the present invention to provide a method for stabilizing an enzyme-labeled antibody for use in an enzyme immunoassay, hereinafter referred to as "EIA", in particular an enzyme-labeled anti-human interferon-β antibody which may be used for a microassay of the human interferon-β in a living body fluid by EIA.

It is another object of the present invention to provide a freeze-dried composition of an enzyme-labeled anti-human interferon-β antibody whose reduction in enzymatic activity remains minimized even after the storage for a long period of time.

It is still another object of the invention to provide an enzyme immunoassay kit, in particular, a non-competitive EIA kit, which comprises the above-described freeze-dried composition having a preferred stability over a long period of time.

It has been found that the above objects and other objects may be achieved by freeze-drying an enzyme-labeled anti-human interferon-β antibody in the presence of trehalose which is a nonreducing disaccharide.

The present invention, therefore, provides a freeze-dried composition substantially consisting of trehalose and an enzyme-labeled anti-human interferon-β antibody.

The freeze-dried composition according to the present invention exerts a good effect on the storage stability of an enzyme-labeled anti-human interferon-β antibody over a long period of time and is capable of maintaining the activity by not less than 70% at room temperature even after 30 days and by 100% at 4° C. even after 500 days.

The present invention also provides an enzyme immunoassay kit comprising such a freeze-dried composition because the composition having excellent long-term storage stability is advantageously utilized for the immunological microassay of the human interferon-β.

DETAILED DESCRIPTION OF THE PREFERRED EMBODIMENT

Figure 1:
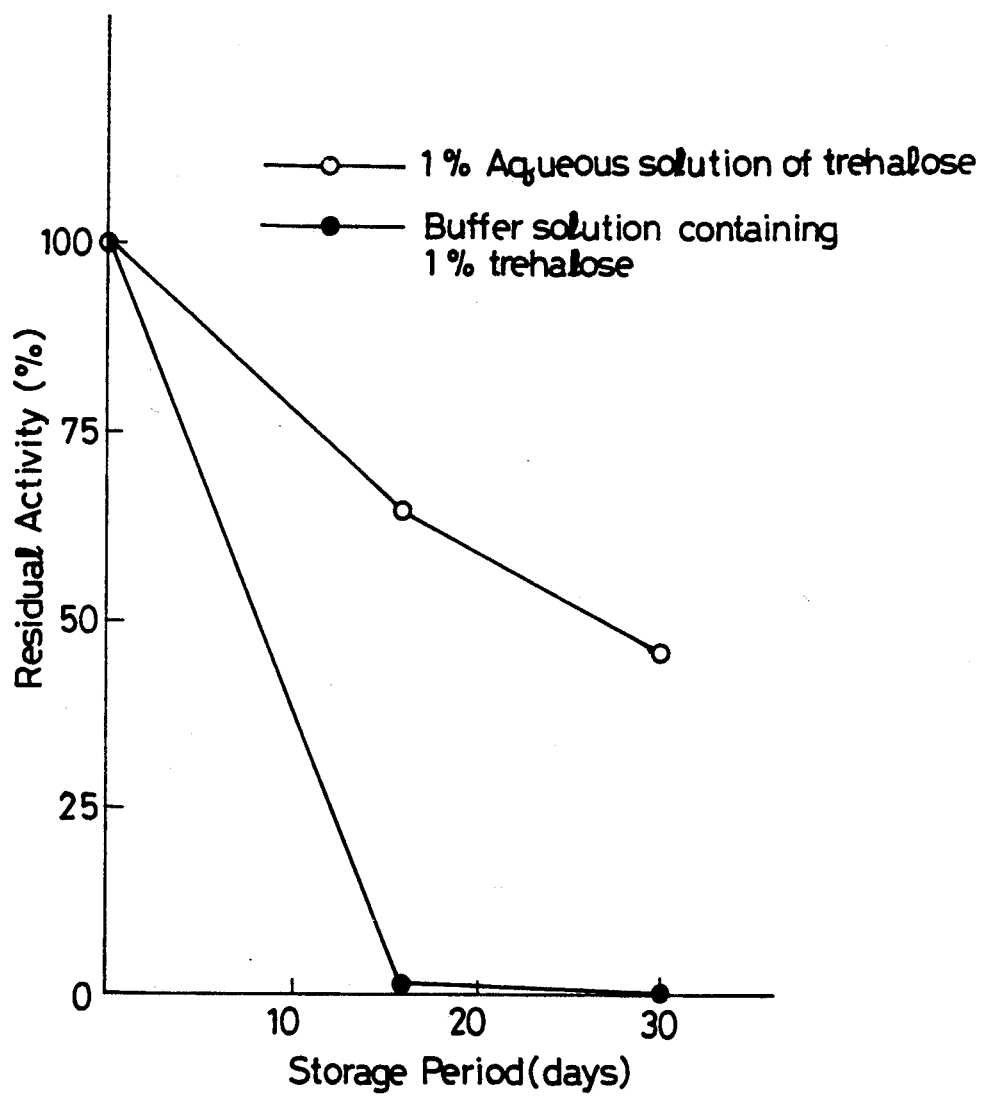
FIG. 1 illustrates a change with the lapse of days at 37° C. in the residual activity of the freeze-dried composition of the enzyme-labeled anti-human interferon-β antibody, in which 1% aqueous solution of trehalose or a buffer solution containing 1% trehalose is contained in an original liquid to be freeze-dried.

The human interferon-β, which is a subject of measurement in the present invention, includes a natural human interferon-β produced by human diploid cells and a recombinant human interferon-β produced by a microorganism such as *Escherichia coli* and yeast or by animal cells such as hamster and monkey, in which the structural gene of the human interferon-β has previously been recombined using a recombinant DNA technology.

For the immunoassay measuring the trace amount of the human interferon-β with high sensitivity and high accuracy, a monoclonal antibody which specifically recognizes only the specific antigenic determinant of an antigen molecule is preferably used as an antibody, i.e., an anti-human interferon-β antibody to be labeled by the enzyme. The monoclonal antibody may be produced, for example, by monoclonal antibody-forming cells which are obtained in accordance with a known cell fusion method (e.g., "Monoclonal Antibodies-Hybridomas: A New Dimension in Biological Analysis", edited by Roger H. Kennet, Thomas J. Mckearn, Kathleen B. Bechtol et al., Plenum Press, New York and London, 1980). That is, splenic cells from a mouse, rat etc. which have been immunized by the human interferon-β are fused with myeloma cells having an infinite proliferation potential to obtain hybridomas of the mouse, rat etc. which have both a potential of antibody formation and a proliferation potential, and the target monoclonal antibody-forming cells are then obtained by cloning. The human interferon-β used for immunization may be either of the natural type or of the recombinant type.

If a monoclonal antibody is from an ascites fluid of the mouse or the like which is obtained by proliferating the hybridoma as an ascites type, the monoclonal antibody suitably diluted in protein concentration of approximately 5–500 μg/ml is sufficiently usable. It is also naturally possible to use an immunoglobulin fraction purified from the ascites fluid. When the hybridoma is cell-cultured in vitro to collect the monoclonal antibody, the purity of the monoclonal antibody in protein ingredients is too low as compared with that of the ascites fluid. In such a case, it is necessary to purify and concentrate the immunoglobulin fraction from a supernatant of the in vitro culture by using an ammonium sulfate precipitation, a protein-A column or an affinity column (i.e., antigen column) which uses the human interferon-β as a ligand, and the like. Although in this case bovine immunoglobulins from the bovine serum ingredients which are used for the culture of the hybridoma may sometimes contaminate the above-described immunoglobulin fraction, there is no problem in practical use. Various serum-free culture media have recently been developed (for example, T. H. Chang et al., J. Immunol. Methods, 39 (1980), 369–375), and the use of the hybridoma cultured on such a culture medium is convenient because it may produce the monoclonal antibody in a high purity. The anti-human interferon-β monoclonal antibody of the present invention is preferably obtained from the hybridoma 1H12 strain described in Japanese Patent Application Laid-Open (KOKAI) No.59-144796. The disclosures of Japanese Patent Application Laid-Open (KOKAI) No.59-144796 are hereby included as reference.

As the monoclonal antibody of the present invention, a Fab'fragment is preferably used which may be obtained by cleaving the Fc portion by a known pepsin-treatment (Y. Hamaguchi et al. (1979), J. Biochem. 85, 1289–1300) after purified to an immunoglobulin fraction, and then by cleaving reductively with mercaptoethylamine (S. Yoshitake et al. (1979), Scandy J. Immunol. 10, 81–86).

Then, the resulting antibody is labeled by an enzyme. For the preparation of the enzyme-labeled antibody, a known reagent can be used. The reagent having two functional groups, for instance N-(ε-maleimide caproyloxy)succineimide, bismaleimide, glutaraldehyde, carbodiimide and the like, or an aldehyde group obtained by oxidizing the saccharide of peroxidase with periodic acid may be effectively used. By using such a reagent, the enzyme is labeled by a conventional method while maintaining the reactivity of the antibody. A preferred enzyme-labeling method used in the present invention is to bind the antibody Fab' having a free Cys residue to a maleimide-bound peroxidase.

The freeze-dried composition according to the present invention is generally prepared by mixing 0.01–1 μg of the enzyme-labeled antibody with 0.5–10% aqueous trehalose solution to obtain an original liquid to be freeze-dried, and then by freeze-drying the original liquid by a conventional method. The trehalose is α-D-glucopyranosyl-α-D-glucopyranoside, which is a disaccharide considered to naturally occur in a living body in relation to the protection of cells.

The freeze-dried composition according to the present invention substantially contains only the trehalose and the enzyme-labeled antibody, but not a substance which disturbs the storage stability. In the case of adding a conventional buffer solution such as a phosphate buffer solution into the original liquid to be freeze-dried, the salts and the like from the buffer solution remain in the composition after freeze-drying and disadvantageously disturb the storage stability. However, a volatile buffer such as ammonium bicarbonate buffer can be added into the original liquid to be freeze-dried because such a buffer, even if it is added into the original liquid, does not disturb the storage stability after freeze-drying.

The thus-prepared freeze-dried composition comprising the enzyme-labeled anti-human interferon-β antibody according to the present invention retains the enzyme activity thereof stable over a long period of time and can be advantageously utilized for an enzyme immunoassay kit to quantitatively determine a trace amount of human interferon-β.

An EIA kit according to the present invention comprises: (a) a solid phase reagent prepared by binding an anti-human interferon-β antibody, which is a first antibody, to a solid phase carrier; and (b) a freeze-dried composition substantially comprising an anti-human interferon-β antibody, which is an enzyme-labeled second antibody, and trehalose.

As the first antibody, a polyclonal antibody may be used which is obtained from antiserum of a human interferon-β-immunized animal. More specifically, the conventional antiserum which is obtained by immunizing an animal such as mouse, guinea pig, rat, rabbit, goat, sheep, horse etc. with a preparation (not necessarily a pure preparation) containing the human interferon-β in accordance with the usual method is preferably purified and concentrated as an immunoglobulin fraction by the usual method before use.

The purified conventional antibody is bound to, for example, a 96-wells microplate, then blocked with bovine serum albumin, casein, gelatin or a commercially available blocking agent, treated with a solution containing polyvinyl pyrrolidone and sucrose, and dried to obtain a solid phase reagent of the microplate.

The second antibody, which is an enzyme-labeled anti-human interferon-β antibody described above in detail, is freeze-dried in the presence of trehalose as described hereinbefore.

The EIA kit according to the present invention is conveniently used for a non-competitive sandwich method.

The procedure for the sandwich method, in which the freeze-dried composition of the enzyme-labeled antihuman interferon-$\beta$ antibody according to the present invention is used, is described hereinafter.

(A) The first antibody directed against the interferon-$\beta$, which is a substance to be measured, forms the solid phase thereof on a carrier. As the carrier, any carrier may be used which is generally used in the sandwich system of immunoassay. Some examples of the carrier include a microplate which is commercially available as an immunoassay plate, plastic beads or iron beads coated with a plastic, glass beads, a plastic tube, a paper disk, cross-linked dextran particles, cross-linked agarose particles, and the like. As a method for forming the solid phase of the first antibody on such a carrier, such a method as physical adsorption and chemical linkage may appropriately be selected in accordance with the carrier to be used.

(B) The sample to be measured is brought into contact with the first antibody on the solid phase, and then the human interferon-$\beta$ to be measured is bound to the first antibody by an antigen-antibody reaction. The conditions (temperature, time etc.) for contact may appropriately be adjusted.

(C) Then, the freeze-dried enzyme-labeled second antibody dissolved in the buffer is brought into contact therewith and is subsequently bound to the human interferon-$\beta$ which has been bound to the first antibody by the antigen-antibody reaction. In this way, the human interferon-$\beta$ is sandwiched between the first and the second antibodies. The conditions (temperature, time etc.) for contact may also appropriately be adjusted.

It is also possible to effect a one-step process in which the steps (B) and (C) are carried out simultaneously. That is, the coexistence of a sample to be measured and the second antibody is capable of sandwiching the human interferon-$\beta$ between the first and the second antibodies. In addition, the measurement with higher sensitivity is expected from the one-step process.

Labelling is carried out with an enzyme by a conventional method. The enzyme generally used includes alkaline phosphatase, $\beta$-galactosidase, a peroxidase such as horseradish peroxidase and the like. The experimental procedures are described in detail in some literature (for example, "Enzyme Immunoassay" edited by Ishikawa, Kawai, Miyai et al., Igakushoin, 1978, Tokyo; "Selected Methods in Cellular Immunology" edited by B. B. Mishell, S. M. Shiigi et al., Freeman and Comp.: 1980, San Francisco; "Fluorescent Antibody Techniques and their Applications" vol. 2 edited by A. Kawamura, Univ. Tokyo Press, 1977, Tokyo), and so it is easy to know the method for preparing the labeled antibody in accordance with the object.

(D) The human interferon-$\beta$ sandwiched between the first and the second antibodies is quantified by measuring the amount of the second antibody. For example, in using an enzyme-labeled second antibody, the decomposition of an added enzyme substrate by the enzyme reaction is measured by colorimetry. If a calibration curve is formed by using the human interferon-$\beta$ having known concentrations, it is possible to know a target concentration of the sample.

Examples of the sample include a culture liquid, a biological material such as a body fluid and urine, and the like. Human serum or plasma may also be used, and IFN-$\beta$ present in human blood is also measurable. The level of the endogenous IFN-$\beta$ has been reported to vary in the blood of patients infected with various viruses such as HIV, HB, HTLV-1 and HTLV-2, and accordingly the assay kit according to the present invention is expected as a diagnostic reagent for AIDS, hepatitis, ATL or the like.

The present invention is further illustrated with the aid of the following non-limited Example.

EXAMPLE

A freeze-dried composition of an enzyme-labeled antibody for use in an enzyme immunoassay of human interferon-$\beta$, which is excellent in storage stability:

An enzyme-labeled antibody was prepared and human interferon-$\beta$ was measured in accordance with the method described in Japanese Patent Application Laid-Open (KOKAI) No.62-206447.

a) Preparation of an enzyme-labeled antibody:

To a mouse anti-human interferon-$\beta$ monoclonal antibody disclosed in Japanese Patent Application Laid-Open (KOKAI) No. 59-144796, 4% pepsin based on the weight of the antibody was added to digest the antibody at 37° C. for 20 hours, and then a F(ab')$_2$ fragment thereof was obtained by a gel filtration through a Sephacryl S-200 column. The fragment thus obtained was reduced by mercaptoethylamine, and then a Fab' fragment was obtained by a gel filtration through a Sephacryl S-200 column. On the other hand, N-($\epsilon$-maleimidecaproyloxy)succineimide was added to horseradish peroxidase, hereinafter referred to as "HRP", reacted at 30° C. for 60 minutes, and then fractionated by passing through a Sephadex G-25 column to obtain maleimide-bound HRP. The antibody Fab' prepared in the above, in an amount of 1.5 mg, was added to 1.2 mg of the maleimide-bound HRP and then reacted at 4° C. for 20 hours. An enzyme-labeled antibody, HRP-antibody Fab', was then obtained by a gel filtration through a Ultrogel AcA-44 column.

b) Measurement of human interferon-$\beta$:

After a polyclonal antibody, which had been affinity-purified from a rabbit anti-human interferon-$\beta$ antiserum, was bound to a microplate, the plate was treated with a PBS solution containing 4% polyvinyl pyrrolidone and 10% sucrose and then dried. Thereafter, the plate was washed once with the buffer containing a detergent, and 100 $\mu$l of a sample containing human interferon-$\beta$ and 50 $\mu$l/well of the enzyme-labeled antibody diluted appropriately, which had been prepared in the above, were added thereto and reacted at 2° to 10° C. overnight. The plate was washed on the next day, and then 100 $\mu$l/well of an enzyme substrate liquid consisting of a phosphate-citrate buffer solution, (pH 5.0), which contains 40 mg of o-phenylenediamine and 20 $\mu$l of aqueous hydrogen peroxide, was added thereto and reacted for 60 minutes at room temperature at a dark place. The reaction was then stopped by adding 100 $\mu$l/well of 4.5N sulfuric acid as a reaction terminator, and an absorbance of the reaction product was measured at a wavelength of 490 nm using 405 nm as reference.

c) Stability of the freeze-dried composition according to the present invention:

The stability of the freeze-dried composition containing the enzyme-labeled antibody prepared in the below way was measured by following the measurement described in the foregoing.

6 μl (about 0.2 μg) of the enzyme-labeled antibody prepared in a) was charged into a 10-ml brown vial, and then 1 ml of 1% aqueous solution of trehalose or a buffer solution (0.1M phosphate buffer, pH 7.0) containing 1% trehalose was added thereto. Two different mixtures were separately freeze-dried to obtain two kinds of freeze-dried composition. When an enzyme immunoassay of human interferon-β was carried out, the freeze-dried composition in a vial was dissolved in 6 ml of buffer solution (0.1M phosphate buffer, 0.1% bovine serum albumin (BSA), 0.05% Tween-20, pH 7.0), and then 50-μl portions of the solution were added to each well for the measurement b). These two kinds of the freeze-dried compositions containing the enzyme-labeled antibody were stored at 37° C. for 30 days in order to compare the storage stabilities between the two. There was no difference between the residual activities of two different freeze-dried compositions, when measured immediately after the freeze-drying. A change in the storage stability was indicated by the residual activity on an assumption that the activity determined immediately after the freeze-drying was 100%. The results are shown in FIG. 1.

As shown in FIG. 1, the residual activity of the freeze-dried composition containing the buffer solution was very low on the 16th and the 30th days, while the freeze-dried composition substantially comprising trehalose and the enzyme-labeled antibody exhibited a prominent effectiveness on the storage stability.

d) Quantitative determination of the human interferon-β:

Use of the freeze-dried composition of the enzyme-labeled antibody according to the invention makes possible a highly sensitive measurement of human interferon-β. The result of measurement which was obtained in accordance with the measurement b) using the serial dilutions (200 μl each) of human interferon-β is shown in FIG. 2.

Figure 2:
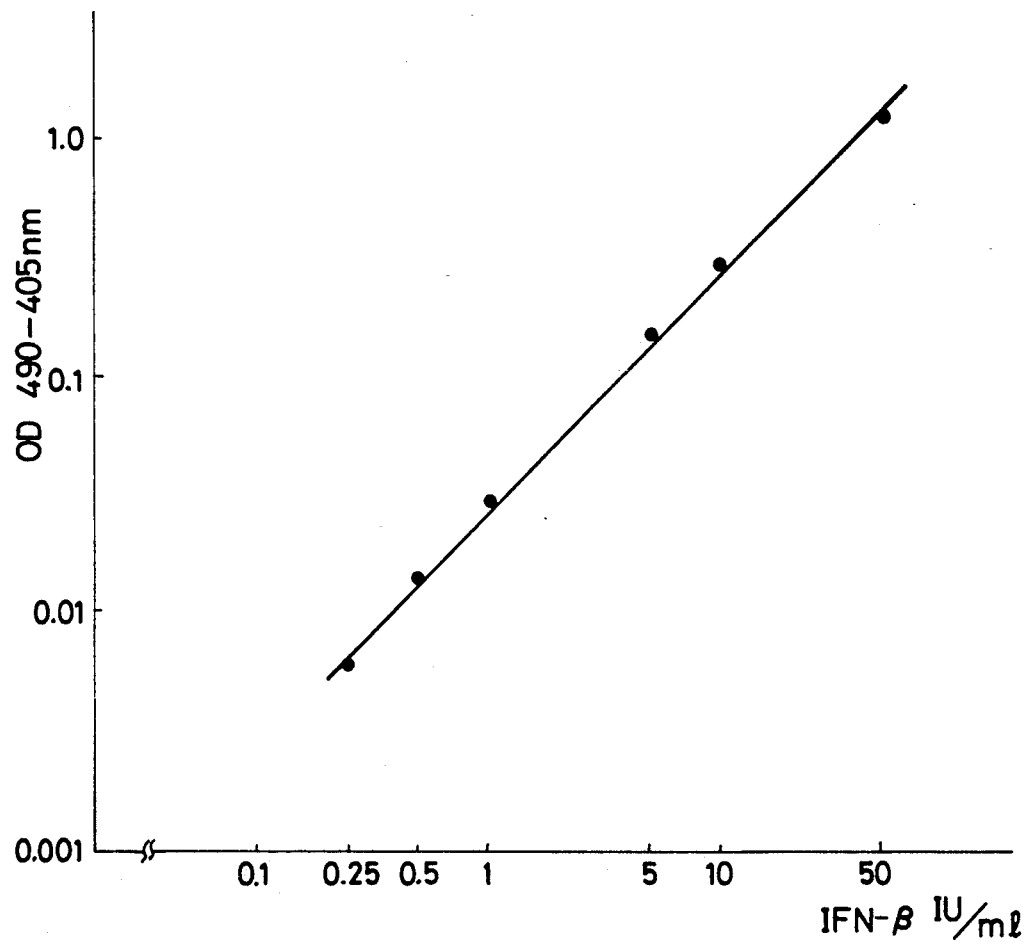
FIG. 2 shows a calibration curve of the enzyme immunoassay according to a sandwich method, which was obtained by measuring the serial dilutions (200 μl each) of standard human interferon-β with the freeze-dried composition of the present invention.

In the calibration curve shown in FIG. 2, the line is linear between 0.25 IU/ml and 50 IU/ml, and the concentration of measurable limit was 0.25 IU/ml. The sensitivity of the measurement is not less than 20 times as high as that of a bioassay. Thus, the method of the present invention is effective for the measurement of the endogenous IFN-β in human blood and may provide important information on a relationship between an etiology and an IFN-β level in the human blood.

We claim:

1. A freeze-dried composition consisting of an enzyme-labeled anti-human interferon-β antibody and trehalose.

2. A freeze-dried composition according to claim 1, wherein the anti-human interferon-β antibody is a monoclonal antibody.

3. A freeze-dried composition according to claim 1 or claim 2, wherein the anti-human interferon-β antibody is a mouse anti-human interferon-β antibody.

4. A freeze-dried composition according to claim 1 or claim 2, wherein the anti-human interferon-β antibody is a Fab' fragment.

5. A freeze-dried composition according to claim 1 or claim 2, wherein the enzyme is horseradish peroxidase.

6. An enzyme immunoassay kit comprising:
   (a) a solid phase reagent prepared by binding an anti-human interferon-β antibody as the first antibody to a solid phase carrier; and
   (b) a freeze-dried composition consisting of an enzyme-labeled anti-human interferon-β antibody as the second antibody and trehalose.

7. An enzyme immunoassay kit according to claim 6, wherein the solid phase reagent is obtained by binding the first antibody to the solid phase carrier and then drying.

8. An enzyme immunoassay kit according to claim 6 or claim 7, wherein the solid phase reagent is obtained by binding the first antibody to the solid phase carrier, treating with a solution containing polyvinyl pyrrolidone and sucrose, and then drying.

9. An enzyme immunoassay kit according to claim 6 or claim 7, wherein the first antibody is a polyclonal antibody.

10. An enzyme immunoassay kit according to claim 6 or claim 7, wherein the first antibody is a rabbit anti-human interferon-β antibody.

11. An enzyme immunoassay kit according to claim 6 or claim 7, wherein the second antibody is a monoclonal antibody.

12. An enzyme immunoassay kit according to claim 6 or claim 7, wherein the second antibody is a mouse anti-human interferon-β antibody.

13. An enzyme immunoassay kit according to claim 6 or claim 7, wherein the second antibody is a Fab' fragment.

14. An enzyme immunoassay kit according to claim 6 or claim 7, wherein the enzyme for labeling of the second antibody is horseradish peroxidase.

* * * * *